(12) United States Patent
Stoddard et al.

(10) Patent No.: US 9,986,314 B1
(45) Date of Patent: May 29, 2018

(54) SYSTEM AND METHOD FOR CONTROLLING AUTHENTICATION OF A PHYSIOLOGICAL ACQUISTION DEVICE BY A PATIENT MONITOR

(71) Applicant: General Electric Company, Schenectady, NY (US)

(72) Inventors: Nathaniel Frederic Stoddard, Milwaukee, WI (US); Todd Weyenberg, Milwaukee, WI (US); David Hernke, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 0 days. days.

(21) Appl. No.: 15/359,165

(22) Filed: Nov. 22, 2016

(51) Int. Cl.
*H04Q 9/00* (2006.01)
*A61B 5/0402* (2006.01)
(Continued)

(52) U.S. Cl.
CPC ............. *H04Q 9/00* (2013.01); *A61B 5/0022* (2013.01); *A61B 5/01* (2013.01); *A61B 5/02055* (2013.01);
(Continued)

(58) Field of Classification Search
CPC ........................................................ H04Q 9/00
See application file for complete search history.

(56) References Cited

U.S. PATENT DOCUMENTS 5,400,267 A    3/1995  Denen et al.

6,298,255 B1   10/2001 Cordera et al.
(Continued)

FOREIGN PATENT DOCUMENTS

WO        2015065568 A1    5/2015

OTHER PUBLICATIONS

Krawczyk, H. HMAC: Keyed-Hashing for Message Authentication [Memorandum]. Network Working Group, RFC 2104.
(Continued)

*Primary Examiner* — Joseph Feild
*Assistant Examiner* — Pameshanand Mahase
(74) *Attorney, Agent, or Firm* — Andrus Intellectual Property Law, LLP (57) ABSTRACT

A patient monitor includes a data connector configured to connect to a corresponding data connector of an approved physiological data acquisition device to provide data transmission to and from the approved physiological data acquisition device, and a power connector configured to connect to a corresponding power connector of the approved physiological data acquisition device to provide power to the approved physiological data acquisition device. The patient monitor further includes a control module configured to detect connection of a corresponding power connector of an unidentified device at the power connection port and/or a corresponding data connector of the unidentified device to the data connector, and provide a limited power amount to the unidentified device through the power connector. The control module performs an authentication process to determine that the unidentified device is the approved physiological data acquisition device, and then provides a full power amount through the power connector to the approved physiological data acquisition device.

20 Claims, 4 Drawing Sheets

(51) Int. Cl.
*H02J 7/00* (2006.01)
*A61B 5/00* (2006.01)
*A61B 5/1455* (2006.01)
*A61B 5/0205* (2006.01)
*A61B 5/01* (2006.01)
*A61B 5/0476* (2006.01)
*A61B 5/08* (2006.01)

(52) U.S. Cl.
CPC .......... *A61B 5/0402* (2013.01); *A61B 5/0476* (2013.01); *A61B 5/14551* (2013.01); *A61B 5/742* (2013.01); *A61B 5/082* (2013.01); *H04Q 2209/40* (2013.01); *H04Q 2209/88* (2013.01)

(56) References Cited

U.S. PATENT DOCUMENTS

| | | |
|---|---|---|
| 7,728,548 B2 | 6/2010 | Daynes et al. |
| 2009/0295326 A1* | 12/2009 | Daynes ................ A61N 1/3975 320/106 |
| 2011/0208013 A1* | 8/2011 | Phan ...................... A61B 5/002 600/301 |
| 2012/0088983 A1* | 4/2012 | Jung ...................... G06F 3/014 600/301 |
| 2014/0223037 A1* | 8/2014 | Minoo .................. G06F 1/1632 710/16 |
| 2015/0039053 A1* | 2/2015 | Kaib .................. A61N 1/37258 607/60 |
| 2015/0235065 A1* | 8/2015 | Brumer .............. G06K 7/10336 340/870.07 |
| 2017/0187699 A1* | 6/2017 | Gillmore ............... H04L 63/062 |

OTHER PUBLICATIONS

International Search Report and Written Opinion for International Application No. PCT/US2017/061980 dated Feb. 2, 2018, 11 pages.

* cited by examiner

SYSTEM AND METHOD FOR CONTROLLING AUTHENTICATION OF A PHYSIOLOGICAL ACQUISTION DEVICE BY A PATIENT MONITOR

BACKGROUND

The present disclosure generally relates to medical patient monitoring systems, and more particularly to methods and systems for authenticating approved physiological data acquisition devices for connection to a patient monitor.

Patient monitors for monitoring physiological data often comprise a central patient monitor connectable to multiple auxiliary devices that acquire physiological data from the patient so that multiple different types of physiological data acquired by multiple different devices is collected and channeled through a central monitoring device. The central monitoring device often includes a display to display the patient physiological data, memory to store the patient physiological data, and/or a transmitter to transmit the patient physiological data to a central network for storage in a patient's electronic medical record. The patient monitor may be connectable with one or more of several different physiological data acquisition devices simultaneously, which could include a pulse oximeter (SPO2), a non-invasive blood pressure monitor (NIBP), an end-title CO2 (EtCO2) monitor, an electrocardiograph (ECG) device, an electroencephalograph (EEG) device, a temperature monitor, an invasive blood pressure monitor, a capnograph, or the like.

Patient monitors and physiological data acquisition devices come in regular contact with patients and must meet high standards of safety and reliability. Since patient monitors may be connected to various different physiological data acquisition devices, it is important to ensure that all physiological acquisition devices connected to the patient monitor are approved as meeting the appropriate quality and safety standards for device performance so that monitoring quality and patient safety are not compromised.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a patient monitor includes a data connector configured to connect to a corresponding data connector of an approved physiological data acquisition device to provide data transmission to and from the approved physiological data acquisition device, and a power connector configured to connect to a corresponding power connector of the approved physiological data acquisition device to provide power to the approved physiological data acquisition device. The patient monitor further includes a control module configured to detect connection of a corresponding power connector of an unidentified device at the power connection port and/or a corresponding data connector of the unidentified device to the data connector, and provide a limited power amount to the unidentified device through the power connector. The control module performs an authentication process to determine that the unidentified device is the approved physiological data acquisition device, and then provides a full power amount through the power connector to the approved physiological data acquisition device.

One embodiment of a method for controlling authentication of an approved physiological data acquisition device by a patient monitor includes detecting connection of a corresponding power connector of an unidentified device to the power connector and providing a limited power amount to the unidentified device through the power connector. The method further includes performing an authentication process to determine that the unidentified device is the approved physiological data acquisition device, and then providing a full power amount through the power connector to the approved physiological data acquisition device.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

The present inventors have recognized that systems and methods are needed for reliably and safely operating patient monitoring devices, including patient monitors that are connectable with various physiological data acquisition devices. Unauthentic devices may not meet the rigorous safety or quality standards set for medical monitoring devices. The inventors have recognized that physiological data acquisition devices must be verified and validated for use in a clinical environment with a patient monitor, both to ensure patient safety and to ensure quality and reliability of the acquired physiological data. In situations where a patient monitor may be connected with any number of data acquisition devices, including unauthentic or unapproved devices, manufacturers of such patient monitors need a way to ensure that only approved devices—and thus devices that meet high quality and safety standards—are connected to the patient monitor.

Based on their recognition of the aforementioned problems and needs, the inventors developed the disclosed system wherein the patient monitor limits the amount of power available to any device connected thereto until that device has been verified as an approved physiological data acquisition device. For example, the limited power amount may be a restricted amount that ensures patient safety until such time as the unidentified device is confirmed to be an approved physiological data acquisition device. Further, the limited power amount may be an amount that is just sufficient to operate the identification aspects of the unidentified device and is not an amount sufficient to operate the physiological data acquisition aspects of the device, thus guaranteeing patient safety and that unreliable data is not acquired or transferred to the patient monitor. The patient monitor may further block any patient data from being displayed by the patient monitor, and may further prevent any physiological data from being stored on any memory of the patient monitor. Likewise, the patient monitor may prevent transmission of any physiological data from unapproved devices via wired or wireless transmission means to any other devices or networks, such as to a host network of a medical facility.

The authentication process may include any of various verification and validation steps. For example, the authentication process may include receiving an identification code from a device and comparing the identification code to a list of acceptable identification codes prior to determining that an unidentified device is an approved physiological data acquisition device. Alternatively or additionally, the authentication process may include operation of a hash function, whereby each of the patient monitor and unidentified device have the same hashing algorithm that each device uses to create a hash result. The calculated results of both devices are compared by the patient monitor to authenticate the device.

For example, upon connection of an unidentified device, the patient monitor may communicate a hash key to the unidentified device. The patient monitor then processes the hash key with the hashing algorithm to create a monitor hash result. Presumably, if the unidentified device is an approved physiological data acquisition device, the device also processes the hash key with the same hashing algorithm to create a device hash result, which it communicates to the patient monitor. The patient monitor receives the device hash result from the unidentified device and compares the device hash result to the monitor hash result. If the hash results match, then the unidentified device is determined to be an approved physiological data acquisition device. At that point, a full power amount is supplied to the approved physiological data acquisition device, and patient monitoring commences.

If the unidentified device does not present a device hash result that matches the monitor hash result, then the operation of the device is not approved. In that case the patient monitor may continue to limit the available power to the unidentified device or may terminate power supplied to the unidentified device altogether. Alternatively or additionally, the patient monitor may continue to block physiological data from the unidentified device and/or prevent display or transmission of the physiological data. Alternatively or additionally, the patient monitor may generate an alert regarding the authentication failure, which may include generating an auditory alarm or providing a visual alert to a clinician operating the patient monitor.

Aspects of the disclosure are described herein in terms of functional and/or logical block components and various processing steps. It should be appreciated that such block components may be realized by any number of hardware, software, and/or firmware components configured to perform the specified functions. For example, an embodiment may employ various integrated circuit components, e.g., memory elements, digital signal processing elements, logic elements, look-up tables, or the like, which may carry out a variety of functions under the control of one or more processors or other control devices. In addition, those skilled in the art will appreciate that the present invention may be practiced in conjunction with any number of medical devices, including any number of different physiological data acquisition devices, and that the system described herein is merely one example application. The connecting lines shown in the various figures contained herein are intended to represent example functional relationships and/or physical couplings between the various elements. It should be noted that many alternative or additional functional relationships or physical connections may be present in a practical embodiment.

Figure 1:
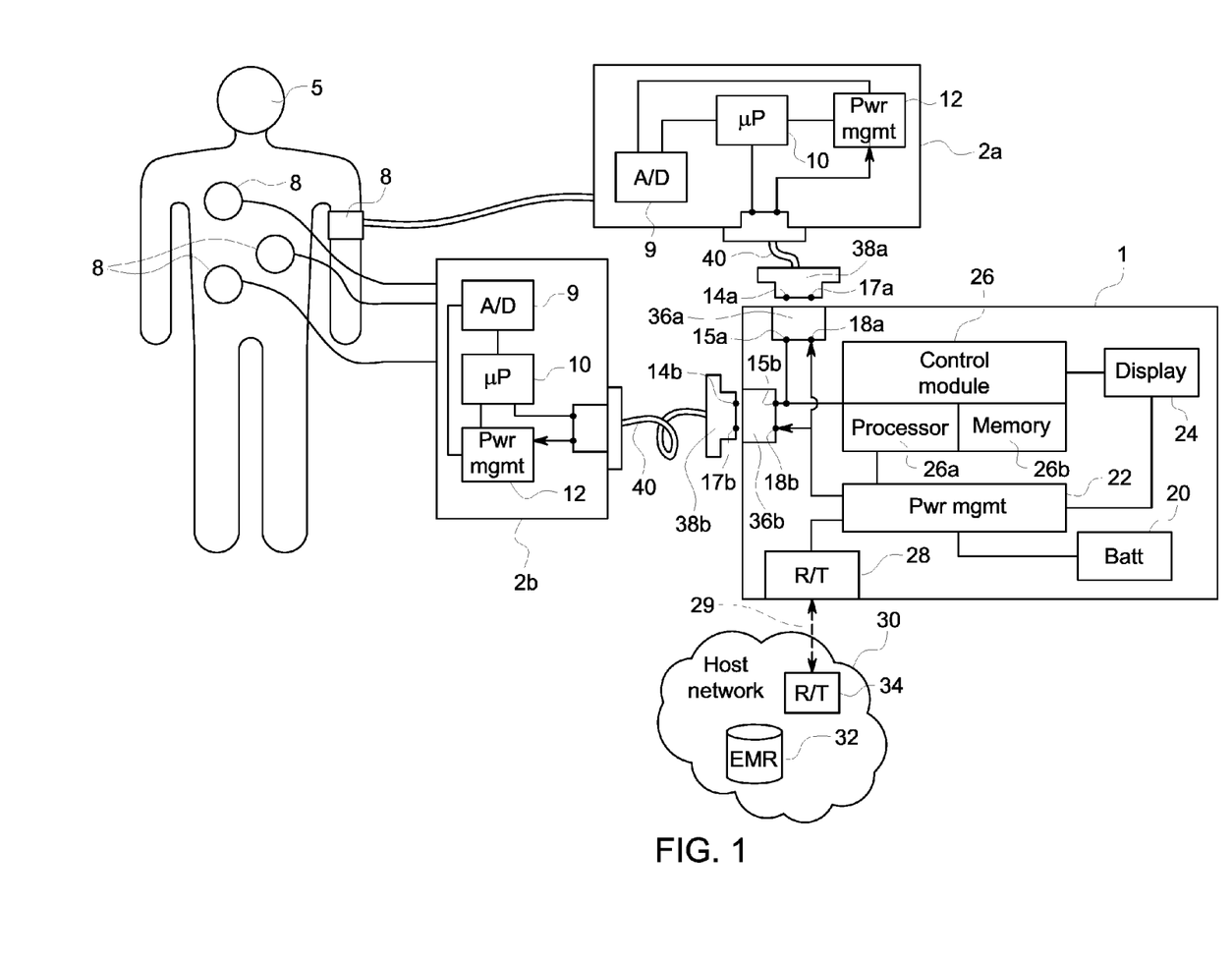
FIG. 1 depicts a patient monitor and physiological data acquisition devices according to one embodiment of the present disclosure.
Figure 2:
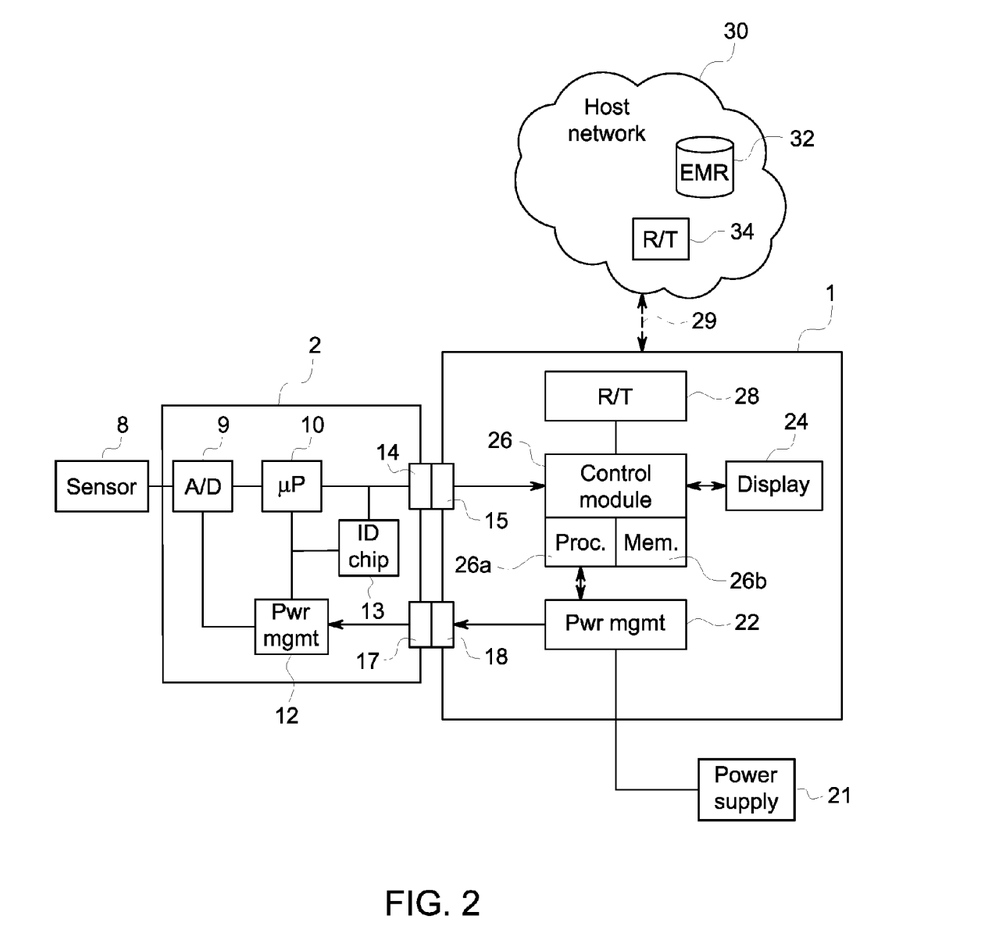
FIG. 2 depicts another patient monitor connected to a physiological data acquisition device according to one embodiment of the present disclosure.

FIGS. 1 and 2 provide block diagrams of differing embodiments of a patient monitor 1 connectable to one or more approved physiological data acquisition devices 2a, 2b. The patient monitor 1 is generally configured to connect to any approved physiological data acquisition device 2, which may include multiple different types of data acquisition devices, such as a pulse oximeter, an NIBP monitor, an EtCO2 monitor, an ECG, an EEG, a temperature monitor, or the like. In the depicted embodiment, the approved physiological data acquisition devices 2a, 2b include an NIBP monitor 2a and an ECG 2b. Each physiological data acquisition device 2 employs one or more sensors 8 connected to the patient 5 to gather the physiological data from the patient 5. In the depicted embodiment, the NIBP monitor 2a has a sensor 8 that is a blood pressure cuff. The ECG device 2b gathers cardiac data through sensors 8 in the form of surface electrodes on the patient's chest and abdomen. These and other types of physiological data acquisition devices are well known and standard in the field of medical patient monitoring.

The patient monitor 1 connects to the approved physiological data acquisition devices via a respective data connector 15a, 15b on the patient monitor 1. Each data connector 15a, 15b is configured to connect to a corresponding data connector 14a, 14b on the approved physiological data acquisition device 2a, 2b. Thereby, data can be transferred in both directions between the patient monitor 1 and the respective approved physiological data acquisition device 2a, 2b. The patient monitor 1 also has on or more power connectors 18a, 18b configured to connect to a corresponding power connector 17a, 17b on the respective approved physiological data acquisition device 2a, 2b to transfer power from the patient monitor 1 to the respective approved physiological data acquisition devices 2a, 2b.

The data connector 15 and power connector 18 may provide an electrical contact or any other connection that allows data communication and power transfer, respectively. For example, the data and power connectors 15 and 18 and the corresponding data and power connectors 14 and 17 may be Universal Serial Bus (USB)-compliant connectors. Alternatively, the connectors 14-15 and 17-18 may be a custom medical USB connector designed for use in a clinical environment.

In alternative embodiments, one or more of the connections may be through means not requiring galvanic contact between the patient monitor 1 and the physiological data acquisition device 2. For example, the data connector 15 and corresponding data connector 14 may be optical devices configured to transfer data via optical data transfer means. Alternatively, the data connector 15 and corresponding data connector 14 may be wireless communication devices operating on any of various radio frequency communication protocols, such as Bluetooth, Bluetooth Low Energy, near field communication (NFC), ANT, or according to any of various wireless network protocols, such as on the wireless medical telemetry service (WMTS) spectrum or on a WiFi-compliant wireless local area network (WLAN). The power connector 18 may also provide connection with the corresponding power connector 17 by means other than through galvanic contact, such as via capacitive or inductive power transfer.

The respective connectors may include control and other circuitry for facilitating the data and power transfer. For example, the data connector 15 may include a universal asynchronous receiver/transmitter (UART), and thus may include an integrated circuit to translate data between parallel and serial forms. Alternatively, the data connector 15 and the corresponding data connector 14 may include $I^2C$ for serial peripheral interface (SPI) communication bus devices.

As depicted in FIG. 1, the data connector 15 and the power connector 18 may be provided in a single connection port 36a, 36b that receives a single corresponding connection element 38a, 38b containing both a corresponding data connector 14a, 14b and a corresponding power connector 17a, 17b. In certain embodiments, one or more cords 40 may be provided with the physiological data acquisition device 2 and may provide the corresponding data connector 14 and/or the corresponding power connector 17, which may be connected and disconnected from the respective connectors at the patient monitor 1.

Alternatively, as depicted in FIG. 2, the data connector 15 and the power connector 18 may be provided in separate and distinct connector ports and connector elements that are independent of one another. As explained above, certain embodiments may require physical connection between the respective connectors of the patient monitor 1 and the approved physiological data acquisition device 2; other embodiments may only require that the devices be in proximity with one another.

The physiological data acquisition device 2 may include any sensor 8, which may include any lead, electrode, lead wire, or available physiological measurement device such as a blood pressure cuff, a pulse oximetry sensor, a temperature sensor, or other device available in the art for acquiring or detecting physiological information from a patient.

The physiological signals recorded by the sensors 8 are digitized by an analog-to-digital converter (A/D converter) 9 in the approved physiological data acquisition device 2. The A/D converter 9 may be any device or logic set capable of digitizing analog physiological signals. For example, the A/D converter 9 may be an analog front end (AFE). The approved physiological data acquisition device 2 may include a processor 10, such as a microprocessor or a microcontroller, that receives the digital physiological data from the A/D converter 9 and oversees transmission of the digitized physiological data to the patient monitor 1 via the corresponding data connector 14. The processor 10 may further execute instructions, such as computer readable software code, which may process the digital physiological data, and the processed data may be transmitted alone or in addition to the raw digitized physiological data from the A/D converter 9. In an alternative embodiment, the physiological data acquisition device 2 may not include any processor. In such an embodiment, the digitized physiological data is sent from the A/D converter 9 to the corresponding data connector 14 for receipt by the patient monitor 1. Accordingly, the patient monitor 1 may be configured to receive digitized raw data, digitized filtered data, processed data, or any other form of physiological data from the physiological data acquisition device 2.

The physiological data acquisition device 2 is powered by the patient monitor 1, and such power is received via the connection between the corresponding power connector 17 and the power connector 18 of the patient monitor 1. The power may be supplied via a galvanic connection between the corresponding power connector 17 and the power connector 18, or through inductive or capacitive coupling, as is described above. The processor 10 and the A/D converter 9 receive power via the power management module 12. The power management module 12 distributes the power to the various powered elements of the physiological data acquisition device 2. For example, the power management module 22 may include voltage and current regulation circuitry and associated controllers. The power management module 12 may include a battery that stores energy received from the patient monitor 1. In other embodiments, where the physiological data acquisition device 2 contains only simple components, such as for a simple temperature sensor, the power management capabilities may not be necessary and may be excluded from the physiological data acquisition device 2.

The power supplied to the physiological data acquisition device 2 is controlled by the power management module 22 in the patient monitor 1. For example, the power management module 22 may include voltage and current regulation circuitry and associated controllers. In the depicted embodiment, the power management module 22 is controlled by and responsive to the control module 26 of the patient monitor 1, which instructs the power management module 22 to limit the power amount provided to an unidentified device until such time as that unidentified device is verified to be an approved physiological data acquisition device 2. Thus, the control module 26 and the power management module 22 cooperate to regulate the power distribution within the patient monitor and the power supplied to the one or more physiological data acquisition devices 2. The managed power may be from a battery 20 or from a power supply 21, such as an AC power supply in the medical facility building. For example, the power management module 22 may provide a limited power amount at an available current of 50 milliamps to an unidentified device. Such a limited current ensures safety of the unidentified device, as it eliminates concern about an improper or unsafe data acquisition device discharging current and injuring a patient 5. Generally, the limited power amount should be a restricted amount that ensures patient safety until such time as the unidentified device is confirmed to be an approved physiological data acquisition device 2 that can be safely operated for patient monitoring in conjunction with the patient monitor 1. Further, the limited power amount may be an amount that is just sufficient to operate the identification aspects of the unidentified device and is not an amount sufficient to operate the physiological data acquisition aspects of the device.

Once the authentication process has been successfully completed to determine that the unidentified device is the approved physiological data acquisition device 2, a full power amount can be supplied such that the approved physiological data acquisition device 2 can perform all of its functions, including any one or more of gathering, processing, storing, and displaying physiological data, and transmitting physiological data to the patient monitor 1. To provide just one exemplary embodiment, the full power amount may be an available current of 700 milliamps.

In various embodiments of the authentication process, the processor 10 of the physiological data acquisition device 2 may provide a device identification code to the patient monitor through the wireless or wired connection between the corresponding data connector 14 and the data connector 15. In certain embodiments, the physiological data acquisition device 2 may have an identification chip or element 13 that provides an identification pin to the patient monitor 1. In one example, the identification element 13 may be a passive or active radio frequency identification (RFID) chip, which may be energized or powered by the patient monitor 1 upon connection thereto. In other embodiments, the identification element 13 could be an application specific integrated circuit (ASIC) or other electronic or logic circuit that performs the device end of the authentication process. For example, in embodiments where the authentication process includes a hashing algorithm, the hashing portion of the authentication process may be performed by the identification element 13, which may receive a hash key from the patient monitor 1 and process the hash key with the hashing algorithm to generate the device hash result. Alternatively, the hashing algorithm function may be performed by a processor 10, such as a general purpose processor for the data acquisition device 2. Either the processor 10 or the identification element 13 acts as and/or includes memory upon which the hashing algorithm, or hash function, is stored. Upon receipt of a hash key from the patient monitor 1, the hashing algorithm is accessed and used to calculate the device hash result. For example, the hashing algorithm may be an iterated cryptographic hash function, or message digest functions, such as MD5 and SHA-1. The message authentication using the hash functions may be performed by any mechanism, such as hashed message authentication code (HMAC) described in RFC2104 of the Network Working Group of the Internet Engineering Task Force (IETF).

Likewise, steps may be performed by the control module 26 within the patient monitor 1 as part of the authentication process. For example, the hashing algorithm may be stored in memory 26b and accessible by a processor 26a comprising part of the control module 26. In one embodiment, the control module 26 generates the hash key, which may be any value or string of values that it shares over the data connector 15 with the respective unidentified device or approved physiological data acquisition device 2. The hash key may be communicated to the processor 10 and/or identification element 13 of the physiological data acquisition device 2 (or unidentified device) as described above. For example, the hash key may be a preset value or string of values, or a randomly generated value or string of values. The control module 26 then processes the hash key with the hashing algorithm to create the monitor hash result. It receives the device hash result from the unidentified device, and compares the device hash result to the monitor hash result to determine whether they match—e.g., whether the hash results are identical or at least a predetermined portion of the results are identical.

In the embodiment of FIGS. 1 and 2, the control module 26 of the patient monitor 1 receives the digital physiological data transmitted from each of the one or more approved physiological data acquisition devices 2a, 2b connected thereto. The control module 26 may be configured to process the digital physiological data prior to transmitting the data to a host network 30 or displaying the physiological data on a display 24 incorporated in or associated with the patient monitor 1. In other embodiments, the control module 26 may not process the digital physiological data, and may simply relay that data to the host network 30, such as via a wireless connection or transmission means. For example, the host network 30 may be a computer network of a hospital, which may be comprised of locally-housed servers or may be a hosted or cloud-computing network. The host network 30 may include a patient electronic medical records (EMR) database 32, and thus the patient monitor 1 transmits the physiological data to the host network 30 for storage in the patient's record within the EMR database 32. For instance, the control module 26 may control a receiver transmitter 28, such as a transceiver, which communicates with a corresponding receiver transmitter 34 within the host network via a communication link 29 in order to transmit the physiological data. The receiver transmitter 28 and 34 may communicate by any wireless or wired transmission protocols, several examples of which are listed above.

The display 24 may be any digital display device capable of displaying information about the condition of the patient monitor 1 and/or a connected approved physiological data acquisition device 2, and/or displaying physiological data or a value calculated therefrom. For example, the control module 26 may control the display 24 to display summaries of the physiological data and/or the physiological data signals themselves to the clinician. The display may be associated with and connected to the patient monitor 1, such as a standard computer monitor, or may be incorporated into a housing with the other elements of the patient monitor 1. In certain embodiments, the display 24 may be a touchscreen providing a mechanism for a clinician to exercise user input control.

The systems and methods described herein may be implemented with one or more computer programs executed by one or more processors 26a, which may all operate as part of a single control module 26. The computer programs include processor-executable instructions that are stored on a non-transitory, tangible computer readable medium, such as may comprise the memory 26b. The computer programs may also include stored data, which may also be stored in memory 26b. Non-limiting examples of the non-transitory tangible computer readable medium are nonvolatile memory, magnetic storage, and optical storage.

As used herein, the term module may refer to, be part of, or include an application-specific integrated circuit (ASIC), an electronic circuit, a combinational logic circuit, a field programmable gate array (FPGA), a processor (shared, dedicated, or group) that executes code, or other suitable components that provide the described functionality, or a combination of some or all of the above, such as in a system-on-chip. The term module may include memory (shared, dedicated, or group) that stores code executed by the processor. The term code, as used herein, may include software, firmware, and/or microcode, and may refer to programs, routines, functions, classes, and/or objects. The term shared, as used above, means that some or all code from multiple modules may be executed using a single (shared) processor. In addition, some or all code to be executed by multiple different processors may be stored by a single (shared) memory. The term group, as used above, means that some or all code comprising part of a single module may be executed using a group of processors. Likewise, some or all code comprising a single module may be stored using a group of memories.

Figure 3:
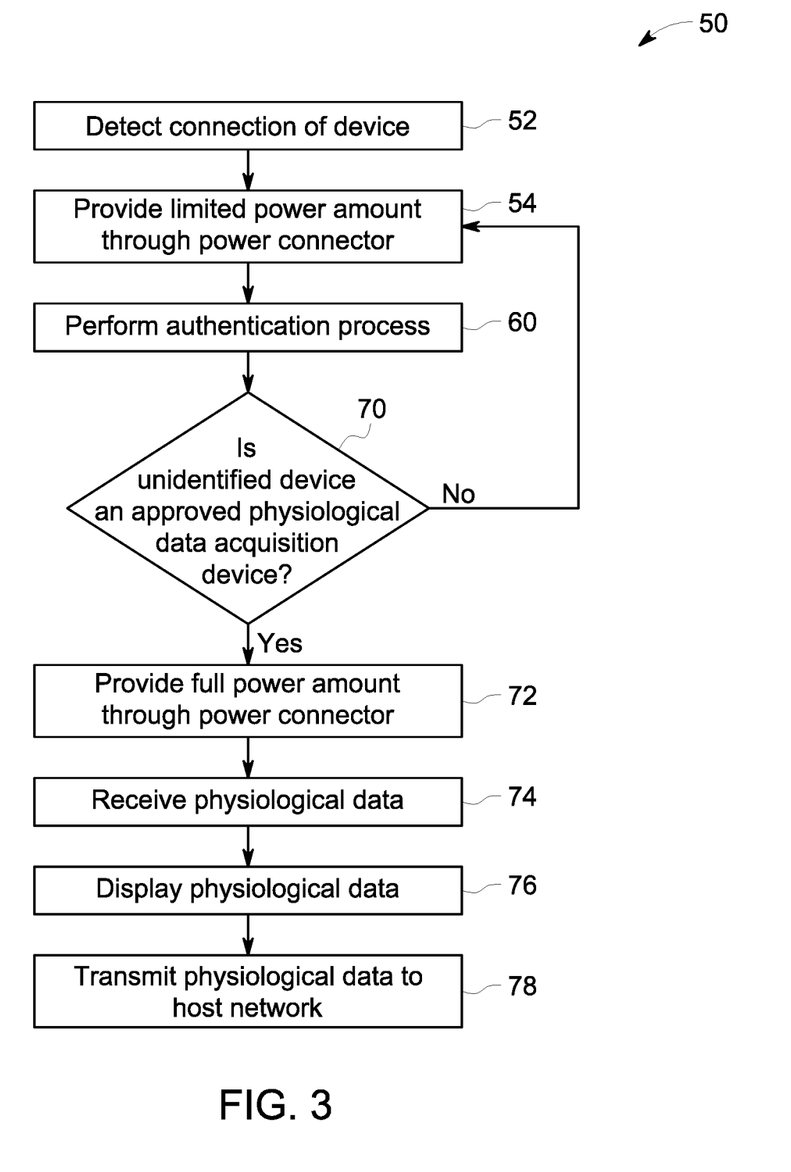
FIG. 3 depicts one embodiment of a method of controlling authentication of an approved physiological data acquisition device by a patient monitor.
Figure 4:
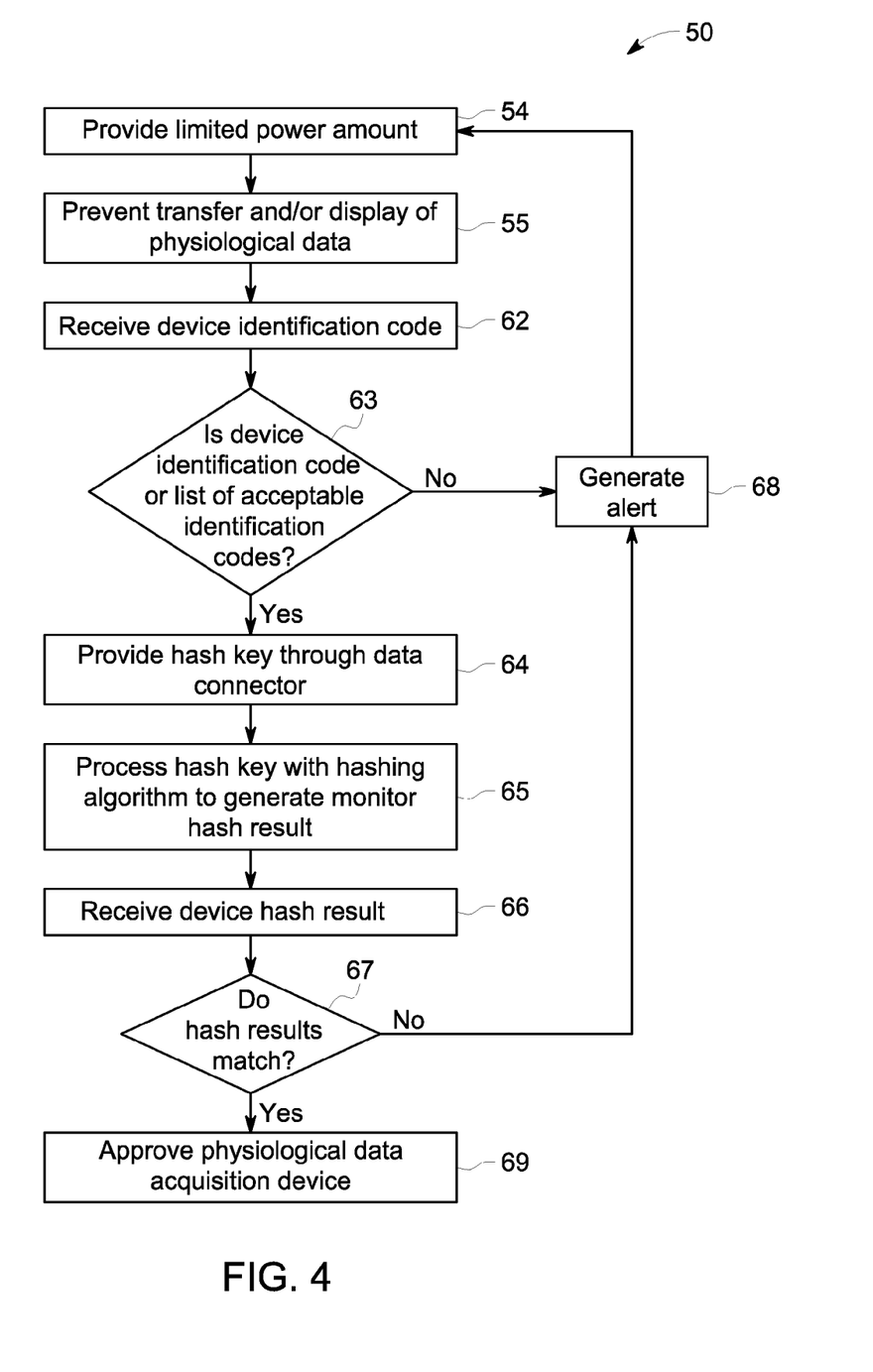
FIG. 4 depicts another embodiment of a method for controlling authentication of an approved physiological data acquisition device by a patient monitor.

FIGS. 3 and 4 depict embodiments of a method 50 for controlling authentication of an approved physiological data acquisition device 2 by a patient monitor 1. Connection of a device is detected at step 52, which is an unidentified device until such time as the device has been authenticated and determined to be an approved physiological data acquisition device 2. A limited power amount is supplied to the unidentified device at step 54, which is supplied by the patient monitor 1 via the connection between the power connector 18 and the corresponding power connector 17. The authentication process is performed at step 60 to authenticate the unidentified device. If the unidentified device is determined to be an approved physiological data acquisition device 2 at step 70, then the full power amount is provided at step 72 so that the approved physiological data acquisition device 2 can perform its data acquisition function. The approved physiological data acquisition device 2 then acquires and digitizes physiological data, which is received by the patient monitor 1 at step 74. The patient monitor displays the physiological data on the display 24 at step 76, and transmits the physiological data to the host network 30 at step 78.

Returning to step 70, if the unidentified device is not an approved physiological data acquisition device, then the limited power amount continues to be provided and no physiological data is displayed or transmitted to the host network. Presumably, the limited power amount is not sufficient for the unidentified device to perform its data acquisition function, which effectively prevents the unidentified device from acquiring the physiological data from the patient in the first place and thus prevents transfer of the physiological data to the patient monitor 1 in the first place. Alternatively or additionally, the patient monitor 1 may take active steps to prevent transfer of data by preventing receipt of data, such as the physiological data, from the unidentified device. In certain embodiments, the limited power amount may continue to be provided to the unidentified device so that further authentication attempts can be made by re-performing the authentication process or performing different authentication steps. In other embodiments, an unidentified device that fails the authentication process once or a predetermined number of times may be cut off completely, including ceasing to supply the limited power amount.

FIG. 4 depicts one embodiment of an authentication process. After the limited power amount is supplied at step 54, active steps may be taken at step 55 to prevent transfer and/or display of the physiological data. The authentication process then commences by receiving an identification code 62 from the unidentified device. The identification code is compared to a list of acceptable identification codes at step 63. If the received device identification code is on the list, then the patient monitor 1 may provide a hash key to the unidentified device, which is communicated through data connector 15 to the corresponding data connector 14. The patient monitor 1 then processes the hash key with the hashing algorithm to generate the monitor hash result at step 65. The device hash result is received at step 66 and compared to the monitor hash result at step 67. If the hash results match then the unidentified device is determined to be an approved physiological data acquisition device at step 69.

If it is determined at step 63 that the received device identification code is not on the list of acceptable identification codes, or it is determined at step 67 that the device hash result does not match the monitor hash result, then an alert is generated at step 68 to advise the clinician that the authentication process failed and that the unidentified device is not an approved physiological data acquisition device. For example, the alert may be a visual alert provided on the display 24 of the patient monitor 1, and/or may include an auditory alert, such as an alarm. The monitor may continue to provide the limited power amount and prevent data transfer, and then re-perform one or more of the authentication steps. Thereby, the patient monitor prevents operation of an unapproved and unidentified device, thereby maintaining control over the safety and quality standards of the physiological data acquisition devices connected to the patient 5.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

We claim:

1. A patient monitor comprising:
   a data connector configured to connect to a corresponding data connector of an approved physiological data acquisition device to provide data transmission to and from the approved physiological data acquisition device;
   a power connector configured to connect to a corresponding power connector of the approved physiological data acquisition device to provide power to the approved physiological data acquisition device;
   a control module configured to:
     detect connection of a corresponding power connector of an unidentified device to the power connector and/or a corresponding data connector of the unidentified device to the data connector;
     provide a limited power amount to the unidentified device through the power connector, wherein the limited power amount is sufficient to power the authentication process by the unidentified device, but is insufficient to power physiological data acquisition by the unidentified device;
     perform an authentication process to determine that the unidentified device is the approved physiological data acquisition device; and
     provide a full power amount through the power connector to the approved physiological data acquisition device so as to power physiological data acquisition by the physiological data acquisition device.

2. The patient monitor of claim 1, wherein the control module is further configured to prevent display of physiological data from the unidentified device to the patient monitor until after it determines that the unidentified device is the approved physiological data acquisition device.

3. The patient monitor of claim 2, wherein the patient monitor:
   receives physiological data from the approved physiological data acquisition device after the control module determines that the unidentified device is the approved physiological data acquisition device; and
   transmits at least a portion of the physiological data to a host network.

4. The patient monitor of claim 3, wherein the patient monitor displays at least a portion of the physiological data from the approved physiological data acquisition device on a display.

5. The patient monitor of claim 1, wherein the control module is configured to:
   provide hash key through the data connector to the unidentified device;
   process the hash key with a hashing algorithm to create a monitor hash result;
   receive a device hash result through the data connector from the unidentified device;

compare the device hash result to the monitor hash result; and determine that the unidentified device is the approved physiological data acquisition device if the device hash result matches the monitor hash result.

6. The patient monitor of claim 5, wherein the control module is further configured to prevent transfer of physiological data from the unidentified device to the patient monitor other than the device hash result until after it determines that the device hash result matches the monitor hash result.

7. The patient monitor of claim 1, wherein the control module is further configured to:

receive a device identification code from the unidentified device; and determine that the device identification code matches one of a list of acceptable identification codes prior to receiving the device hash result from the unidentified device.

8. The patient monitor of claim 1, wherein the data connector and the power connector are provided in a single connection port on the patient monitor that receives a single corresponding connection element containing the corresponding data connector and the corresponding power connector.

9. The patient monitor of claim 1, wherein the data connector is a wireless transceiver in the patient monitor configured to wirelessly connect to the corresponding data connector, which is a wireless transceiver in the approved data acquisition device.

10. The patient monitor of claim 1, wherein the limited power amount is an available current of 50 milliamps.

11. A method for controlling authentication of an approved physiological data acquisition device by a patient monitor, the method comprising:

detecting connection of a corresponding power connector of an unidentified device to the power connector and/or a corresponding data connector of the unidentified device to the data connector;

providing a limited power amount to the unidentified device through the power connector, wherein the limited power amount is sufficient to power the authentication process by the unidentified device, but is insufficient to power physiological data acquisition by the unidentified device;

performing an authentication process to determine that the unidentified device is an approved physiological data acquisition device; and providing a full power amount through the power connector to the approved physiological data acquisition device so as to power physiological data acquisition by the physiological data acquisition device.

12. The method of claim 11, wherein the authentication process includes:

providing hash key through the data connector to the unidentified device;

processing the hash key with a hashing algorithm to create a monitor hash result;

receiving a device hash result through the data connector from the unidentified device;

comparing the device hash result to the monitor hash result; and determining that the unidentified device is the approved physiological data acquisition device if the device hash result matches the monitor hash result.

13. The method of claim 12, further comprising preventing transfer of physiological data from the unidentified device to the patient monitor until after determining that the device hash result matches the monitor hash result.

14. The method of claim 13, further comprising:

receiving physiological data from the approved physiological data acquisition device after determining that the device hash result matches the monitor hash result; and transmitting at least a portion of the physiological data to a host network.

15. The method of claim 14, further comprising displaying on a display in the patient monitor at least a portion of the physiological data from the approved physiological data acquisition device.

16. The method of claim 12, wherein the authentication process further includes:

receiving a device identification code through the data connector from the unidentified device; and determining that the device identification code matches one of a list of acceptable identification codes prior to receiving the device hash result from the unidentified device.

17. The method of claim 12, further comprising:

determining that the unidentified device is not the approved physiological device if the device hash result does not match the monitor hash result;

continuing to provide the limited power amount to the unidentified device through the power connector; and preventing display of physiological data from the unidentified device to the patient monitor.

18. The method of claim 11, further comprising preventing display of physiological data from the unidentified device to the patient monitor until after determining that the unidentified device is the approved physiological data acquisition device.

19. The method of claim 11, wherein the authentication process includes:

receiving a device identification code from the unidentified device; and determining that the device identification code matches one of a list of acceptable identification codes prior to receiving the device hash result from the unidentified device.

20. The method of claim 11, further comprising:

determining that the unidentified device is not the approved physiological device; and continuing to provide the limited power amount to the unidentified device through the power connector; and preventing transfer of physiological data from the unidentified device to the patient monitor.

* * * * *